(12) United States Patent
Fuhr et al.

(10) Patent No.: US 6,841,356 B1
(45) Date of Patent: Jan. 11, 2005

(54) PROCESSES FOR CELL TRACED BASED TESTING OF BIOLOGICAL CELLS

(75) Inventors: Gunter Fuhr, Berlin (DE); Rolf Hagedorn, Berlin (DE); Stephen Graham Shirley, Warkwickshire (GB); Ekkehard Richter, Berlin (DE)

(73) Assignee: Evotec Technologies GmbH, Duesseldorf (DE)

( * ) Notice: Subject to any disclaimer, the term of this patent is extended or adjusted under 35 U.S.C. 154(b) by 0 days.

(21) Appl. No.: 09/868,200

(22) PCT Filed: Dec. 10, 1999

(86) PCT No.: PCT/EP99/09781

§ 371 (c)(1),
(2), (4) Date: Sep. 10, 2001

(87) PCT Pub. No.: WO00/36415

PCT Pub. Date: Jun. 22, 2000

(30) Foreign Application Priority Data

Dec. 14, 1998  (DE) .......................... 198 57 692

(51) Int. Cl.⁷ ............................... C12Q 1/02
(52) U.S. Cl. ........................ 435/29; 435/325
(58) Field of Search .......... 435/4, 29, 287.1, 435/287.9, 325

(56) References Cited

U.S. PATENT DOCUMENTS

| | | | |
|---|---|---|---|
| 4,359,527 A | 11/1982 | Zetter ........................ | 435/29 |
| 5,047,321 A | 9/1991 | Loken et al. ................. | 435/6 |
| 5,962,136 A | 10/1999 | Dewez et al. ............... | 428/410 |

FOREIGN PATENT DOCUMENTS

| | | |
|---|---|---|
| DE | 3119269 | 12/1982 |
| EP | 0 849 595 B1 * | 12/1996 |
| FR | 2743421 | 7/1997 |

OTHER PUBLICATIONS

Chen W. Mechanism of Retraction of the Trailing Edge During Fibroblast Movement. J of Cell Biology 90(1)187–200, 1981.*

Fuhr G. Cell Traces . . . Biol Chem 379(8–9)1161–1173, Aug./Sep. 1998.*

Matsuda T. Control of Cell Adhesion, Migration, and Orientation on Photochemically Microprocessed Surfaces. J of Biomedical Materials Res 32(2)165–173, 1996.*

English translation of FR 2743421 by Ronfard et al.

E.D. Hay et al., "Interaction of Migrating Embryonic Cells with Extracellular Matrix", Expl. Biol. Med., vol. 10, pp. 174–193 (Karger, Basel 1985).

* cited by examiner

*Primary Examiner*—Ralph Gitomer
(74) *Attorney, Agent, or Firm*—Baker Botts LLP (57) ABSTRACT

For the cell trace based testing of biological cells, wherein the cells (16) are applied to an at least partially structured and/or surface modified substrate (11) and move adhesively over surface track regions (13, 15) of the substrate while producing cell traces (14a, 14b) consisting of material residues separated from the cells, cell tests are performed on the cell traces. A process for cell cultivation on biocompatible modified substrates whose surfaces are covered by cell traces is also described.

26 Claims, 6 Drawing Sheets

PROCESSES FOR CELL TRACED BASED TESTING OF BIOLOGICAL CELLS

This application is filed under Rule 371 and claims priority to International Application PCT/EP99/09781 filed Dec. 12, 1999 which claims priority to German application DE 198 57 692.7 filed Dec. 14, 1998.

The invention concerns processes and devices for cell testing, particularly cell assays or cell test arrangements, their production, and processes for their use. The invention also concerns applications of cell traces on substrate surfaces.

SUMMARY OF THE INVENTION

In pharmacology, toxicology, and medical diagnostics, cell-based assays (reaction assays, test assays, or similar assays) assume a key role. Quickly available and highly specific testing and assay processes are desired for biological cells per se or for their interactions with other cells or with natural or synthetic foreign substances. In addition, it would be desirable if the cells used for the detection of a substance, a cell type, the effects of a medication, etc., could be used again (i.e. could be cultivated further). In the medical field, this means, e.g., a reintroduction into the organism of the donor (e.g. a patient) or of another human receptor. However, for these types of procedures, in addition to sterility, very high requirements are placed on the cell properties not being altered due to the testing or analysis. Thus, marking, (e.g. for the generation of fluorescence), as it is used in immunofluorescence using fluorochrome is not permissible, because the secondary reactions of these types of contaminated cells during subsequent cultivation or in the receptor organism can only be assessed with difficulty.

Furthermore, there is interest in performing cell testing specifically on single cells. For a statistically reliable testing result, a sufficiently high number of single cells must be tested. For this reason, there is a need for previously unavailable parallel tests on a number of single cells under conditions which are as uniform is possible.

The object of the invention is to develop extremely low stress processes and devices for cell testing, also usable in the medical field, which can be combined with as many as possible of the highly-specific assay technologies already proven, such as immunofluorescence of proteins, nucleotides, and lipids using fluorochrome, as well as destructive processes, such as x-ray or electron beam microanalysis, and which allow parallel testing of multiple single cells. The object of the invention is also to indicate new applications for cell traces.

The object is achieved by processes and devices with the features according to patent claims 1 and/or 17. Advantageous embodiments and applications of the invention arise from the dependent claims.

Figure 2:
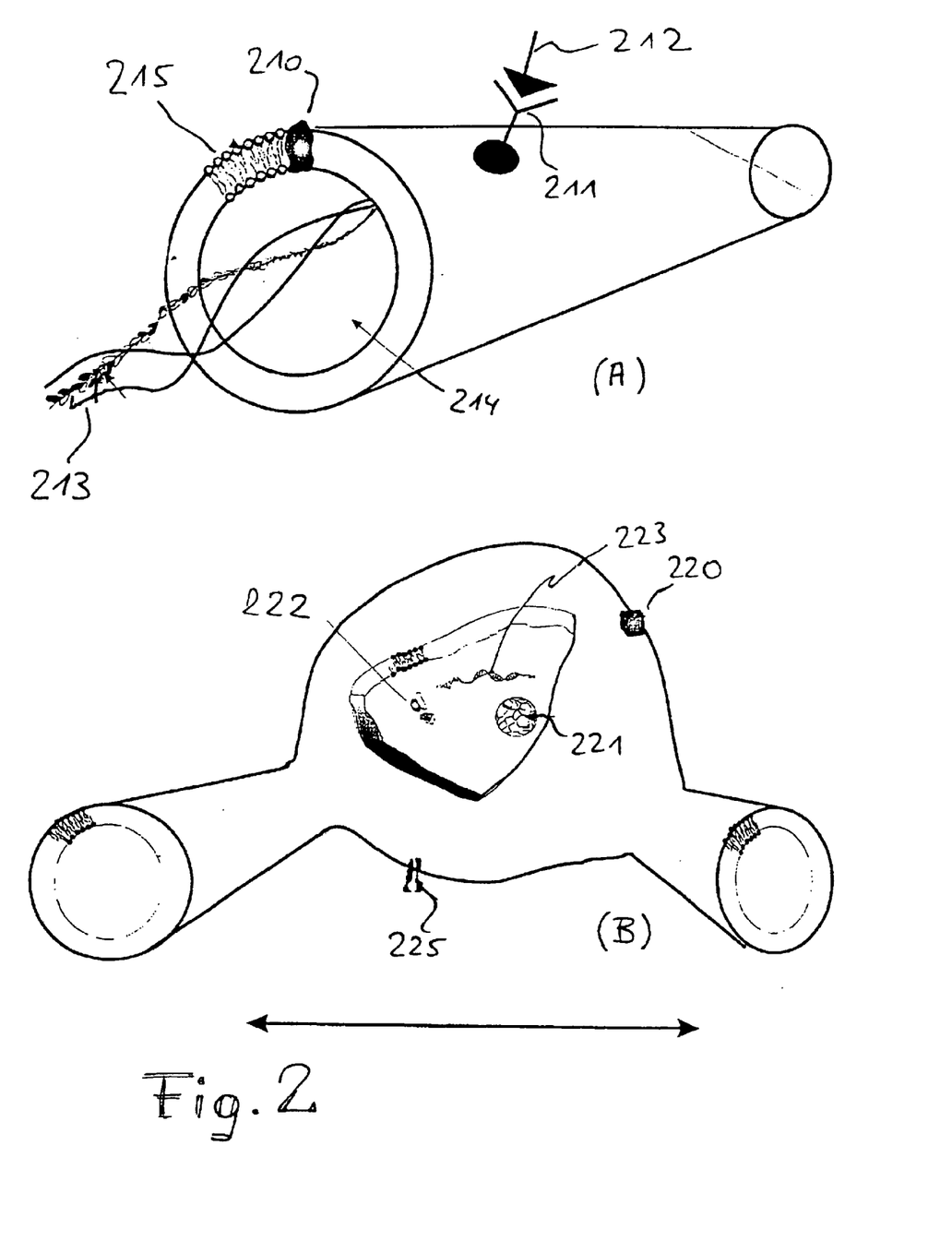

The basic idea of the invention is, in particular, for testing or cultivating of biological cells or their interactions with other cells or substances, first to produce cell traces of the cells to be tested on a substrate surface and then to subject these cell traces to the desired analysis or testing. The production of cell traces through cells which grow or move while adhering to surfaces is known per se and is, for example, described by E. D. Hay et al. in "Exp. Biol. Med.", volume 10, 1985, p. 174 et seq. The structures and properties and cell traces will be explained below with reference to the FIGS. 2 and 3. The production of the cell traces is preferably performed using substrate surfaces which are at least partially microstructured and/or modified in a suitable way. The microstructuring of the substrate surface is particularly provided for the purpose of promoting cell trace production in specific substrate regions, e.g. along specific paths, and impeding or preventing it in other substrate regions. The surface modification further allows not only material traces naturally left on the substrate to be tested, but also artificially separated material residues (achievement of larger trace amounts). For this purpose, the substrate modification particularly comprises the application of molecules offering the specific binding sites on which a predetermined cell surface molecule being searched for can couple.

The testing methods used according to the invention comprise all techniques known per se for cell testing and cell treatment, with both nondestructive and destructive techniques, or possibly also biochemical amplification techniques (e.g. PCR process), able to be used.

The subject of the invention is also the use of cell traces for the manipulation of the interaction of biological cells with solid substrates. Through the targeted application of cell traces to synthetic or biological substrates according to the principles explained in the present description, biocompatible carriers for the biological cells to be manipulated are provided. The manipulation particularly consists of targeted cell cultivation (tissue buildup) on the substrate areas coated with cell traces.

The substrate surfaces used according to the invention can consist of synthetic, inorganic, or organic material, or can also be formed by biological material (e.g. bone material).

The invention has the following advantages. For the first time, a process for cell testing specific to single cells is provided in which the cells tested remain unaffected and unchanged by the testing procedure. This allows a significant expansion of the use of single cell testing in pharmacology, toxicology, medical diagnostics, and biochemistry. The cell testing can be performed in parallel to a high degree on multiple cells through simultaneous production of many traces on a substrate. Because an assignment of the cell trace to a tested cell (donor cell) is possible due to the microstructuring on the surfaces, the highly parallel single cell testing also remains cell-specific. The microstructuring of the substrate surface can preferably be performed with techniques known per se from semiconductor processing.

According to the invention, the cells except for the trace production are not stressed by any kind of staining or marking technique. They are thus not contaminated or altered and can be subjected to medical use and/or cryo-preservation or further cultivation. The cell residues are subjected to a specific marking or evaluation, instead of this being done in cells, as was previously the practice. This can definitely also be destructive (e.g. step-by-step enzymatic decomposition) or be performed via immunofluorescence using fluorochrome in toxic concentration ranges.

The cell cultivation according to the invention has the advantage that, with cell traces, any desired substrate material, such as those of interest for the implantation of bone materials, can be made biocompatible. Novel substrates for in vitro tissue buildup are created which have a significantly expanded range of use. Through cell trace-based modification of substrate surfaces, depending on the application, optimized cell cultures can be applied to optimized substrate materials which, without the cell traces, would possibly not be compatible with another.

BRIEF DESCRIPTION OF THE DRAWINGS

Further embodiments and advantages of the invention will be described in the following with reference to the attached drawings. These show.

DETAILED DESCRIPTION OF THE INVENTION

Figure 1:
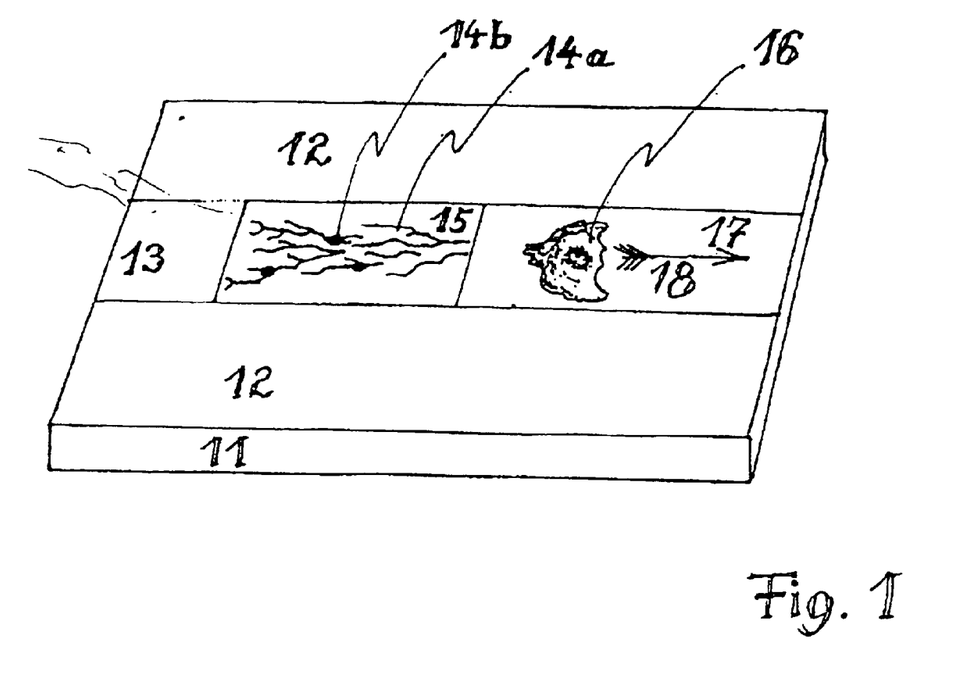
FIG. 1 the design in principle of a cell trace-based system according to the invention (detail), FIG. 2 a schematic illustration of the basic structures of cell traces in the form of filaments (A) and membrane spots (B), FIG. 3 an illustration of the function of a modified substrate, FIG. 4 an illustration of fluorescence testing of cell traces according to the invention FIG. 5 an embodiment of the invention in which the basic principle illustrated in FIG. 1 is realized with multiple parallel tracks, FIG. 6 a further embodiment of the invention with multiple parallel cell tracks, and FIG. 7 a further embodiment of the invention with intersecting cell tracks.

In FIG. 1, the design in principle of a cell trace-based system according to the invention is depicted. A substrate 11 has its surface structured in the $\mu$m and mm range and/or has its surface characteristics changed as follows.

With regions 12 of the surface, on which cells can only poorly adhere, and regions 13, 15, 17 (surface track regions), where cells can adhere well, a preferred track is formed on which a cell 16 can actively move. The field 15 in the surface track region is modified in such a way (chemically, mechanically, etc.) that the cells lose parts of their membrane and inner components 14a, 14b here, which adhere to the substrate. In the example shown, these are filaments 14a and membrane spots (or membrane patches) 14b which are explained in detail below with reference to FIGS. 2A and 2B. The cell moves further in the direction of the arrow 18. The cell trace can now be analyzed destructively or nondestructively. The material left behind characterizes the donor cell both in regard to the membrane composition (receptors, carriers, lipids, etc.), and in regard to internal components of the cytoplasm, from which medical, toxicological, pharmacological, and other applications can be derived. Either a single cell or multiple cells can move on a track and produce traces.

The substrate 11 consists, for example, of glass, mica, inorganic crystalline material, or semiconductor material. The substrate surface is, on one hand, structured and/or modified for the implementation of the preferred track, on which the cell preferably moves and leaves behind cell traces. The surface regions 12, on which the cells can only adhere poorly, have, for example, a coating with negatively charged molecules, preferably made of polymers with as many OH$^-$-groups as possible, such as poly-HEMA. Examples for influencing the regions 13, 15, 17, in which the cells can adhere well, are indicated below. On the other hand, the microstructuring and/or modification of the substrate surface comprises a positionally selective influencing of the preferred track between the regions 12 of the substrate surface. The segmentation of the preferred track, e.g. in the regions 13, 15, and 17, is provided for the purpose of causing the cell traces to be left behind in particularly large or small numbers or in regard to a specific composition, depending on the design of the respective region. This will illustrated in the examples explained below.

The microtexturing and/or modification of the preferred track comprises, for example:

1. Application of films which increase the molecular cell contact (e.g. fibronectin, polylysine, alginate, etc.). The film thickness selected can be, depending on the application, from the thickness of one layer of molecules up to the $\mu$m range. The molecule monolayers are preferably applied with the Langmuir-Blodgett technique. In general, thick-film techniques and/or plasma treatments are also usable for the film application.

2. Nanostructuring and/or microstructuring of surfaces, i.e. application of patterns in nm and/or $\mu$m dimensions, on which membrane parts, but in particular natural contact molecules of the cells, such as those of the integrin and catherin family, can adhere (e.g. structuring via photo or electron beam lithography).

3. Sub-micrometer and atomic roughening or relief formation on surfaces (tiny barbs, etc.).

The substrate charging (application of the cells) occurs, for example, by washing the cells out of a suspension, for example through the channel of the microsystem, with a manipulator (capillary, separate microsystem, or optical tweezers), or also through active growing.

As the cells travel over substrate surfaces (e.g. over a clean glass surface), under physiological conditions, they leave behind filamentary or spot-like traces which will be referred to in the following as filaments or membrane patches, respectively, and will be explained with reference to FIGS. 2A and/or 2B. The traces are, as a rule, structures which are surrounded by a membrane and are filled with cell contents. The typical dimensions of these structures in regard to width and height are in the $\mu$m and sub-$\mu$m range. While the length of a membrane patch essentially corresponds, as a rule, to its width, the length of a filament is variable. The filament length can be up to several mm. The components of interest of the cells, which can also be found in the cell traces, are membrane proteins 210, surface proteins and receptors 211, 212, cytoplasm components 213, 214, and the lipids 215 in the membrane (cf. FIG. 2A). In addition to these components, comprising, e.g., the membrane proteins 220 and the lipid composition 225 in FIG. 2B, vesicles 221, organelles 222, and genetic material 223 also occur in the membrane patches. In addition, cytoplasma 224 is also present. In the framework of the present invention, it was determined for the first time that the cell traces contain a sufficient amount of material capable of being analyzed which contains, among other things, the components mentioned. This means that the analysis or testing processes known per se can be advantageously implemented without separate enrichment steps.

The surface proteins and receptors 211, 212 comprise, for example, a trace protein 211 in the membrane and a coupled receptor 212 with a chromophore group. Fluorescent light is emitted from the receptor 212 upon suitable light excitation, indicating the presence of the trace protein 211. Because the receptor coupling is protein-specific, the protein complexes present in the trace can be determined with fluorescent light.

In an analogous way, other assay techniques can also be implemented, as, for example, they are provided in the ELISA and RIAS assays.

Thus, according to the invention, the specific assay of definite components of the donor cell is performed on the cell traces. The components can be located on the surface of or inside the cell traces. In the latter case, it is provided that the membrane of the cell trace be dissolved with suitable solvents or mechanically or electrically permeated. The destructive measurement of the cell traces to detect molecular or microscopic components in the cell traces, without alteration of the donor cells, represents a particular advantage of the invention.

The cell trace-based analyses are particularly suitable for combination with highly sensitive measurement techniques.

These include, for example, fluorescence correlation analysis for single molecule assay and for determination of binding constants, mass spectrometry for elemental analysis, and confocal laser scanning microscopy. Genetic material in the traces can, e.g., be amplified via a PCR process, whereby a novel technique of genetic analysis, which does not influence the donor cell in its physiological cells, is provided.

For single cell-based assays and assay processes, the following procedures can also be used.

1. The amount of the cell residue is detected as a quantitative dimension for the strength of the adhesion of the donor cell to the substrate surface, and thus for the amount of specific binding complexes in its membrane.
2. The trace structure is detected as a dimension, e.g. the ratios of the portion of filaments to the portion of branches, to the portion of patches, etc. (comparison of the quantities of cell trace base elements).
3. The material composition of the traces is detected as a parameter, e.g. lipid/protein portion, specific occurrence of specific receptors (among others, the immunoglobulin families), specific occurrence of lipids, nucleotides, etc.
4. Characterization of cytoplasmic residues, particularly genetic materials in the residues of the cells.
5. Comparison of changes in one of the points 1 to 4 after treatment of the cells producing the traces (e.g. with pharmaceuticals, toxic substances, etc.).
6. The stability of the trace to mechanical, electrical, acoustical, optical, or chemical treatments is detected as a parameter.
7. The elemental composition of the traces or parts of the composition (e.g. Na, K, P . . . ) is detected as a parameter.
8. Passive electrical parameters of the cell residues, such as impedance, breakthrough resistance, non-linear behavior, and heating, are detected as a parameter.
9. Optical parameters of the traces are detected as a parameter, such as absorption, transmission, non-linear characteristics, etc.
10. Mechanical characteristics of the traces, such as elasticity, plasticity, etc., are detected as a parameter.
11. The alteration of a cell trace by a subsequent cell of the same or a different type is detected as a parameter.
12. The trace characterization is performed after fixing and/or contrasting, e.g. by means of high-resolution microscopy processes (raster electron microscopy, AFM, SNOM, etc.).
13. A negative or another duplicate or a multiplication of trace components, as in the PCR technique, is used as a dimension for the comparison.
14. The adhesion of other materials, such as highly specific binding beads or nm particles, is detected as a parameter for the comparison.

The parameters mentioned here are detected as specific values for the donor cells which are used with given comparison values for characterization of the donor cell or, with comparison of the parameter with the corresponding results from other cells, for characterization of the differing behavior of the cells.

In the following, embodiments of devices according to the invention will be explained with reference to FIGS. 3 to 7. Characteristics of the substrate surfaces used according to the invention will hereby be discussed. Characteristics of an overall apparatus for cell trace testing are not shown, because these are known per se in regard to the handling of assays and/or of substrates charged with samples, and the adjustment to the respective desired testing methods.

Figure 3:
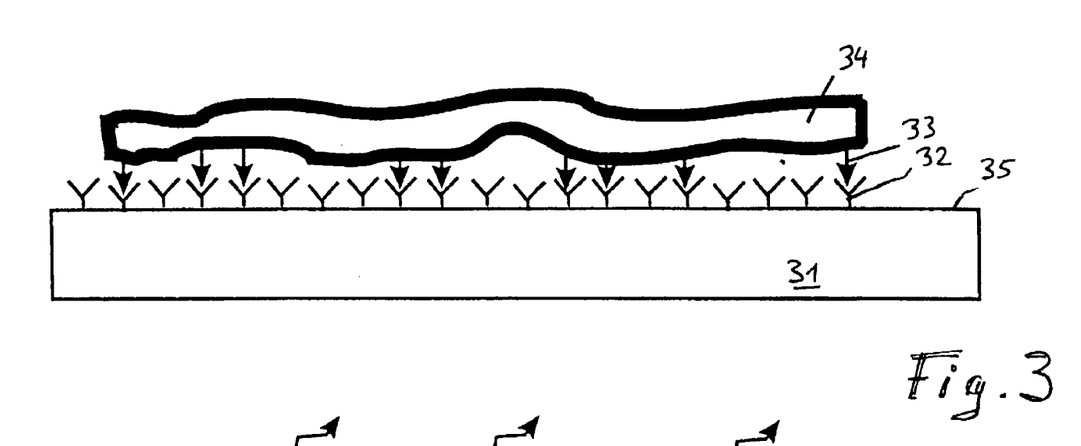
Figure 4:
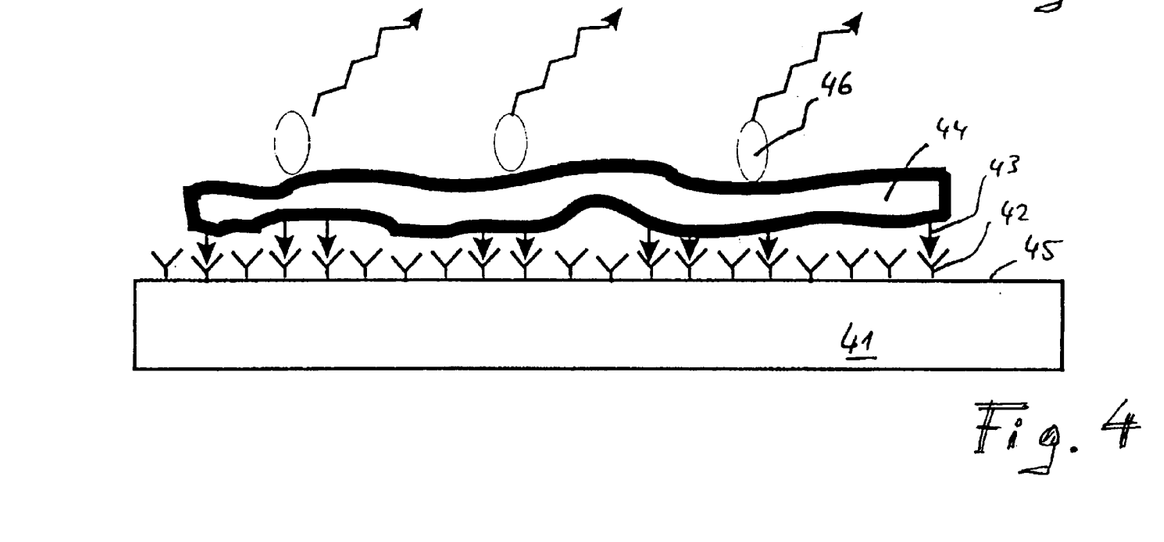

FIGS. 3 and 4 are schematic sectional views of substrates 31, 41, which are each provided with a modification film 32 and/or 42 in the surface track region 35 and/or 45 for preferred adhesion of cells and deposition of cell traces 34 and/or 44. The modification film 32 (and/or 42) offers binding sites on which a predetermined cell surface molecule 33 (and/or 43) which is being sought can couple to specifically. A cell which has a sufficient number of this type of molecule is correspondingly bound more firmly and leaves behind more trace material 34 (and/or 44) as it travels over the substrate compared to other cell types. The detection of the amount of the material left behind (e.g. with optical means) provides an indication of the content of the predetermined cell surface molecule in the cell tested. The cell itself is not stressed by the measurement.

If the amount of the cell trace material is too small for a reliable direct evaluation, the cell trace measurement according to FIG. 4 can be modified. After production of the cell traces 44, they are treated with the solution of a fluorescence marker, which is nonspecifically embedded as a marker molecule 46, e.g., in the lipid part of the cell trace 44. With suitable light excitation and fluorescence measurement, the number of marker molecules 46 and thereby the quantity of amount of the cell trace material 44 can be inferred from the intensity of the fluorescent light.

The preferred track according to FIG. 1 and/or the modified surface track region 35 (or 45) according to FIG. 3 (or 4) can be implemented on the substrate once or multiple times with greatly varying geometries. In the following, straight preferred tracks are described. However, with suitable substrate structuring, curved (e.g. circular) preferred tracks are also possible.

Figure 5:
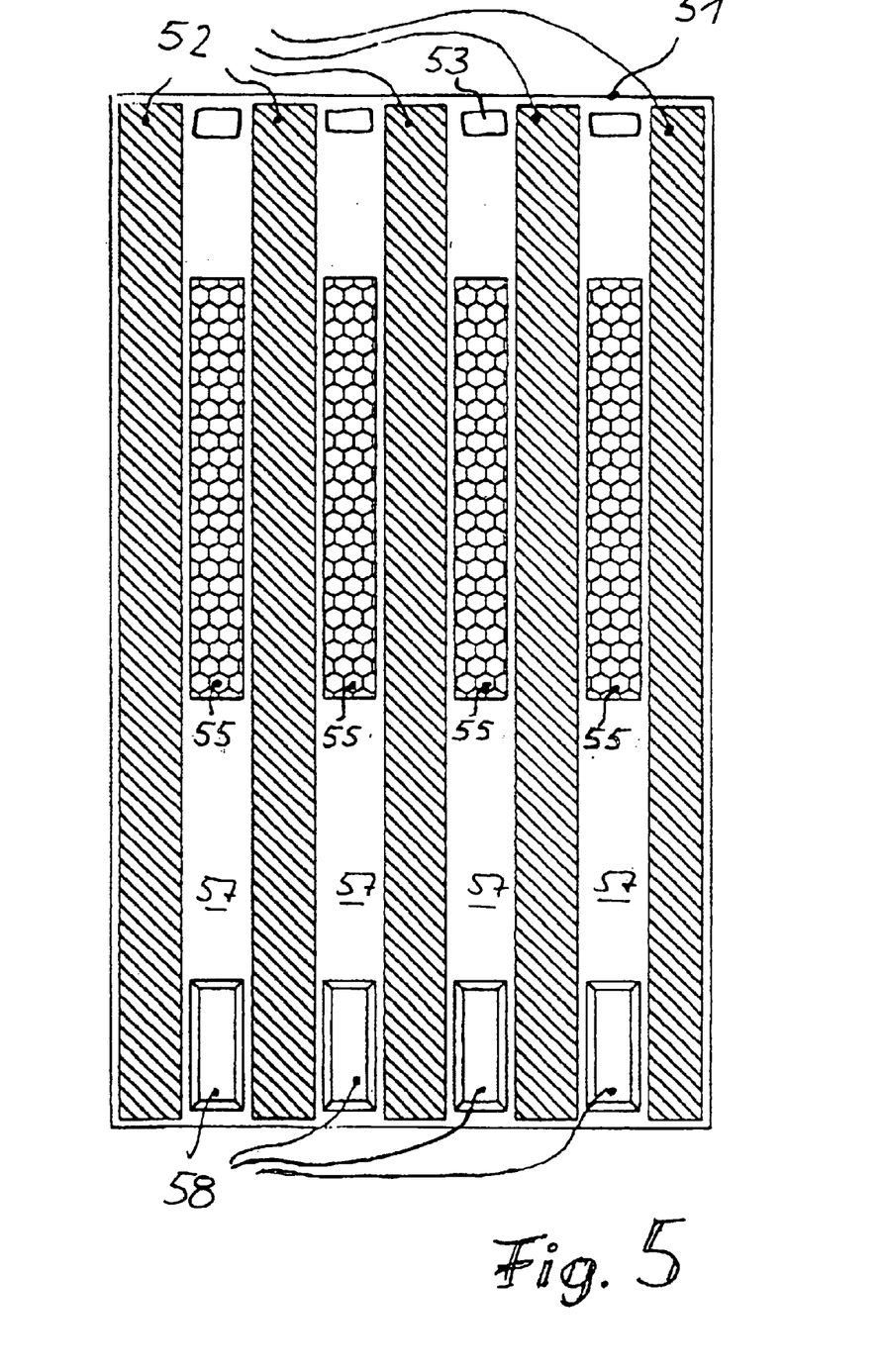

FIG. 5 shows an example of a parallel implementation of the basic principle explained in FIG. 1 with multiple straight preferred tracks running in parallel.

The materials 52 which suppress cell adhesion are applied to a substrate 51, which can consist of, e.g., glass, silicon, or plastic.

Multiple tracks 57 (surface track regions), on which cells can move while adhering, thereby arise. The tracks 57 reach from entrance depots 53 via surface fields 55 to exit depots 58. The surface fields 55 are treated in such a way that cell traces are preferably produced. If the cells reach the exit depots 58, which are also prepared for adhesion, they are fixed there and/or removed in order to be subjected to cultivation, cryopreservation, or another procedure. The analysis of the trace can be performed with all typical microassay processes (fluorescence, isotope marking, elemental analysis, etc.). The surface fields 55 with the cell traces (not shown) are, as segments of the tracks 57, each positioned in a row at the same distance from the respective entrance depot 53. This makes parallel, simultaneous evaluation of the cell traces easier.

Figure 6:
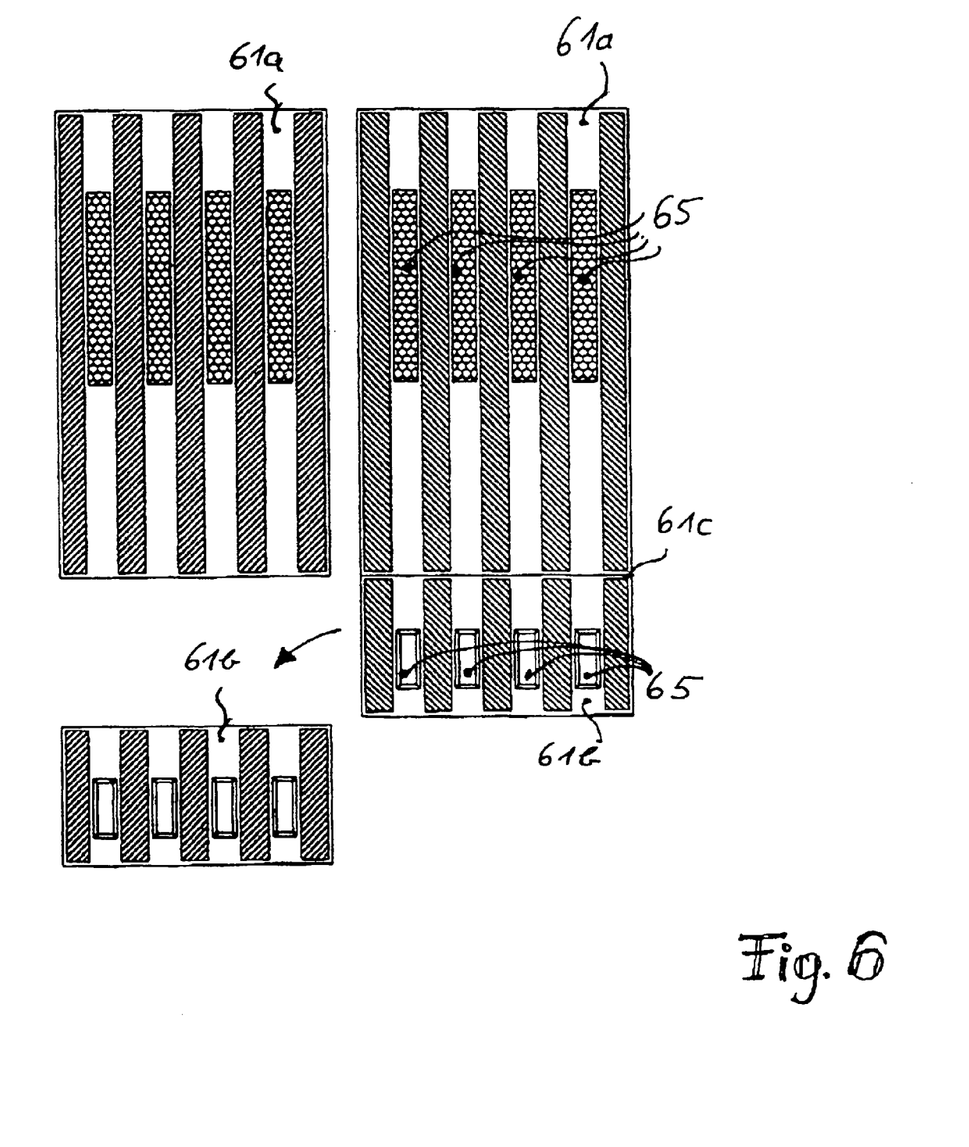

In FIG. 6, a substrate surface in the form of a microsystem is shown which is compartmentalized in a similar way as in FIG. 5 into various surface regions. However, the substrate consists here either of two parts 61a, 61b or one part with a desired fracture point 61c. The cells leave behind traces on the fields 55. If they reach the exit depots 68 as they travel over the substrate, the part 61b is removed or broken off. As is shown in the left part of FIG. 6, the traces and cells are then each on separate substrates 31 and 32, so that they can be further treated in different ways.

Analogous to these embodiments, surfaces can also be produced with many more cell paths, in which the traces of many cells can be produced and characterized in such a way that they can be uniquely assigned.

Figure 7:
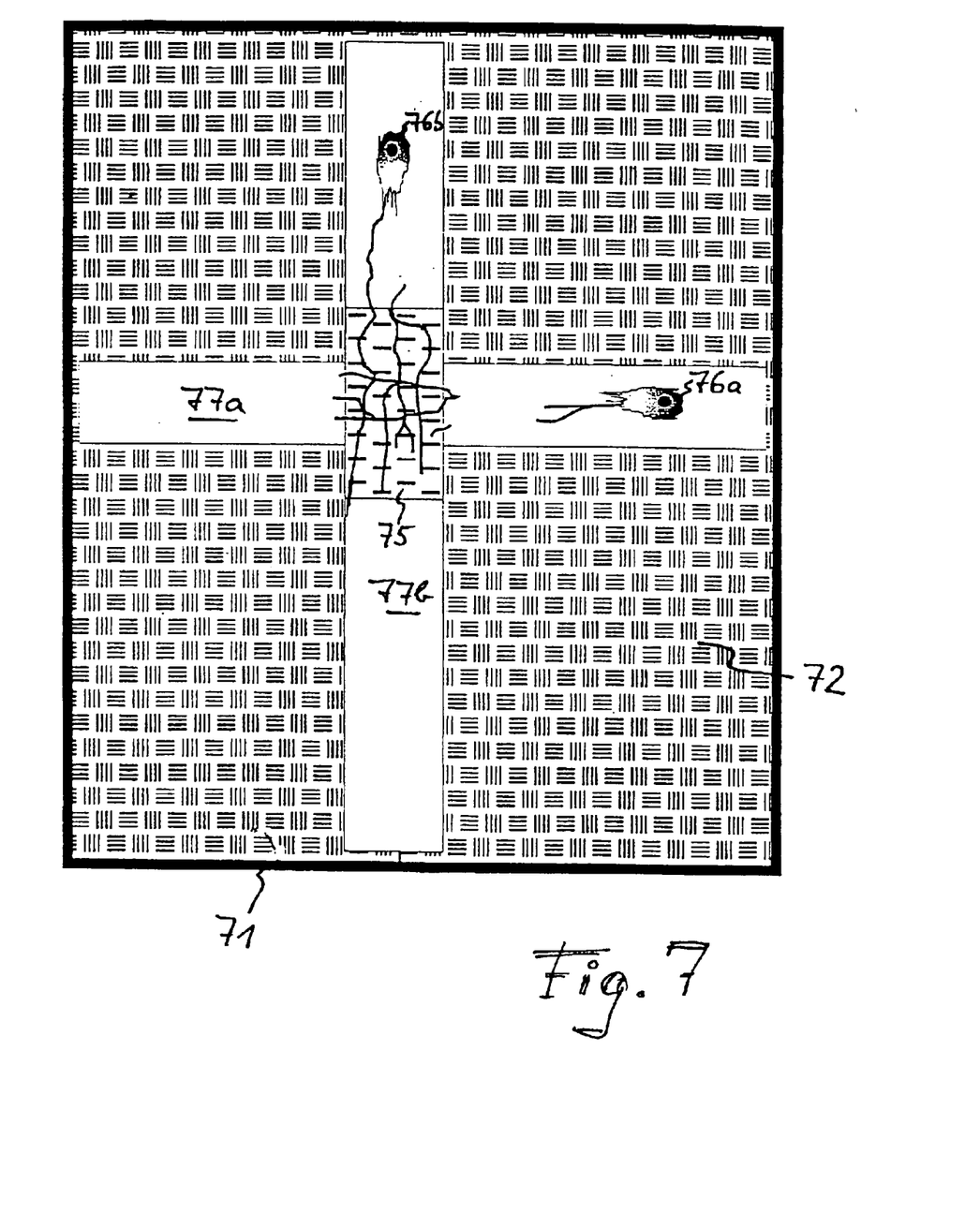

FIG. 7 shows a substrate surface which is structured in such a way that two preferred tracks set up for the traveling of the donor cells intersect. The tracks 77a and 77b run essentially perpendicular to one another on the substrate 71. The surface modification or structuring to encourage the adhesion of cell traces is applied in the intersection region 75, as is described above. Except for the tracks 77a and/or 77b, the substrate 71 is structured in such a way that the cells do not travel and no cell traces adhere there.

Interactions between various cells can advantageously be tested with the arrangement shown in FIG. 7. It can, e.g., be provided that the cell 76a first travels over the region 75 and leaves behind cell traces there. Subsequently, the cell 76b travels over the same region 75 with the cell traces present. With an optical-microscopic process or another testing process, it is then detected whether the traces of the first cell 76 are altered, overlaid, or removed by the second cell 76b. Furthermore, it can be detected whether geometric correlations between the cell traces occur, i.e. if the following cells follow the traces of the preceding cells or avoid them. From this, cell based assays for medicine, biotechnology, and pharmacology with high specificity can, in turn, be developed. A substrate with intersecting tracks can, in turn, be used to implement parallel processing multiple times on a joint carrier.

The production of a substrate according to the invention is preferably performed in such a way that first a carrier material is provided with a coating which is unsuitable for cell travel and adhesion (e.g. strongly negatively charged molecules). This coating is then structured according to the desired course of the preferred tracks by wearing, so that the carrier material is exposed according to specific geometric shapes, which then form the preferred tracks. The preferred track is subsequently segmented depending on the application, i.e. the application of structuring and/or modification of the carrier material for amplified cell adhesion.

The track widths are preferably adjusted to the characteristic dimension of an adherent cell and are approximately 50 $\mu$m. The track lengths can also be selected depending on the application. They are, for example, from 3 to 4 characteristic cell diameters (i.e. approximately 150 to 200 micrometers) up to greater lengths in the mm range.

According to a further embodiment of the invention, cell traces are applied to substrates for cell cultivation. Flat or, depending on the application, curved solid materials of synthetic or biological origins are used as the substrate. For example, glass, ceramic, or plastic materials, or even polished bone disks, are used as the substrate. In order to provide the respective substrate surfaces with a biocompatible coating, tissue producing cells, such as chondrocytes, osteoblasts, or epithelial cells are placed, according to the principles explained above, on the substrate surfaces, in order to travel on them while leaving behind cell traces. The substrate surface can be structured or modified in other ways (see above) for the most extensive possible application of cell traces. After formation of a closed cell trace surface, tissue buildup occurs on the modified substrate. Tissue producing cells, preferably of the type with which the cell traces were produced, are cultivated on the modified substrate. A substrate with cultivated tissue cells is then, depending on the application, used as an implant in the human body.

What is claimed is:

1. A process for cell traced based testing of biological cells wherein said testing identifies at least one property of said cells, wherein the cells to be tested are applied to a substrate, which is at least partially structured and/or surface modified, and move adhesively over the surface track regions of the substrate while producing cell traces, wherein the cell traces consist of material residues separated from the cells as the cells move over the surface track regions and wherein said cell traces are analysed to identify a property of said cells.

2. The process according to claim 1, wherein the amount, the geometry, the chemical composition, the passive electrical parameters, and/or the mechanical properties of the cell traces or of their components are detected for the cell testing.

3. The process according to claim 2, wherein filaments and membrane patches are detected to determine the quantity and geometry of the cell traces.

4. The process according to claim 2, wherein, to detect the composition of the cell traces, the cell traces are subjected to staining or marking for the performance of microanalytic processes.

5. The process according to claim 4, wherein the microanalytic processes comprise fluorescence measurements, measurements on the basis of isotope markings, or elemental analysis.

6. The process according to claim 2, wherein, to detect the composition of the cell traces, the cell traces are subjected to enzymatic decomposition.

7. The process according to claim 2, wherein the cell traces are tested with a high-resolution microscopy process.

8. The process according to claim 2, wherein cytoplasmic residues or genetic materials are detected in the cell traces.

9. The process according to claim 2, wherein the stability of the cell traces during mechanical, electrical, acoustic, optical, and/or chemical treatments is detected.

10. The process according to claim 2, wherein, to determine the passive electrical parameters of the cell traces, the impedance, breakthrough resistance, non-linear behaviour, and/or heating during current flow of the cell traces are detected.

11. The process according to claim 2, wherein, to determine mechanical properties of the cell traces, the elasticity or plasticity of the cell traces is detected.

12. The process according to claim 1, wherein a duplication of components of the cell traces is performed to produce reference material.

13. The process according to claim 1, wherein the cell traces are produced in predetermined surface track regions, which are at least partially microstructured and/or modified for amplified adhesion of the cells.

14. The process according to claim 1, wherein the cells are subjected, after the production of the cell traces, to a medical or measurement technology application, cryopreservation, or further cultivation.

15. The process according to claim 1, wherein multiple cell traces are produced and tested on multiple parallel tracks.

16. The process according to claim 1, wherein cell traces are produced on intersecting tracks and the mutual interactions of the participating cells and/or cell traces are tested at intersection regions of the intersecting tracks.

17. A device for cell trace based testing of biological cells comprising a substrate having surface regions and surface track regions, wherein said cells adhere more poorly on the surface regions than on surface track regions, and wherein the surface track regions are arranged for the adhesion of cell traces consisting of material residues separated from the cells.

18. The device according to claim 17, wherein the substrate is structurally and/or chemically modified in the surface regions and/or the surface track regions, in order to suppress and/or encourage the adhesion of cell traces.

19. The device according to claim 17, wherein the substrate is part of a microsystem on which the surface regions and the surface track regions are implemented, with the surface track regions forming at least one straight track.

20. The device according to claim 17, wherein the substrate consists of glass, silicon, or a plastic.

21. The device according to claim 17, wherein multiple surface track regions in the form of a group of parallel tracks or intersecting tracks are formed.

22. The device according to claim 17, wherein the substrate is in two parts, with the surface track regions located on one of the substrate parts.

23. A process for cell trace based cultivation of biological cells, in which the cells are applied to an at least partially structured and/or surface modified substrate and move adhesively over the surface of the substrate while producing cell traces, wherein the cell traces consist of material residues separated from the cells, and cultivation of the same or a different type of cells is performed on the cell traces.

24. The process according to claim 23, wherein the biological cells are tissue producing cells and the substrate comprises an material to be implanted in the human body.

25. A process of testing of the properties of cells for medical, biochemical, and/or pharmacological purposes, or for biocompatible modification of the surfaces of implant material residues, which are formed by biological cells as cell traces on substrates.

26. A process for the manipulation of biological cells, in which the cells are applied to a substrate, which is at least partially structured and/or surface modified, and move adhesively over surface track regions of the substrate while producing cell traces, wherein the cell traces consist of material residues separated from the cells which contain genetic materials of the cells, and the genetic materials are subjected to amplification and the amplified genetic material is subjected to a genetic analysis.

* * * * *